United States Patent
DiFoggio et al.

(10) Patent No.: US 8,878,548 B2
(45) Date of Patent: Nov. 4, 2014

(54) METHOD FOR TREATING AND SEALING PIEZOELECTRIC TUNING FORKS

(75) Inventors: Rocco DiFoggio, Houston, TX (US); Yi Liu, Houston, TX (US); Louis Perez, Houston, TX (US); Paul Bergren, Houston, TX (US); Kerry L. Sanderlin, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 691 days.

(21) Appl. No.: 13/155,034

(22) Filed: Jun. 7, 2011

(65) Prior Publication Data

US 2011/0304346 A1  Dec. 15, 2011

Related U.S. Application Data

(60) Provisional application No. 61/353,816, filed on Jun. 11, 2010.

(51) Int. Cl.

| | | |
|---|---|---|
| *G01R 27/04* | (2006.01) | |
| *G01N 29/02* | (2006.01) | |
| *H01L 41/053* | (2006.01) | |
| *G01N 29/028* | (2006.01) | |
| *H01L 41/23* | (2013.01) | |

(52) U.S. Cl.
CPC ...... *G01N 29/022* (2013.01); *G01N 2291/0289* (2013.01); *H01L 41/0533* (2013.01); *G01N 2291/02818* (2013.01); *G01N 29/028* (2013.01); *H01L 41/23* (2013.01); *G01N 2291/0427* (2013.01)
USPC .................................................. 324/633

(58) Field of Classification Search
CPC .............. G01N 29/028; G01N 29/022; G01N 2291/0427; G01N 2291/0289
USPC ............................................................ 324/633
See application file for complete search history.

(56) References Cited

U.S. PATENT DOCUMENTS

| | | | |
|---|---|---|---|
| 4,286,216 A * | 8/1981 | Auld et al. .................... | 324/237 |
| 4,876,675 A | 10/1989 | Ogura et al. | |
| 6,076,097 A | 6/2000 | London et al. | |
| 6,182,499 B1 | 2/2001 | McFarland et al. | |
| 6,332,567 B1 | 12/2001 | Ikegami et al. | |
| 6,336,353 B2 | 1/2002 | Matsiev et al. | |
| 6,393,895 B1 | 5/2002 | Matsiev et al. | |
| 6,401,519 B1 | 6/2002 | McFarland et al. | |
| 6,455,315 B1 | 9/2002 | Baszczynski et al. | |

(Continued)

OTHER PUBLICATIONS

Measurement Specialties, "FPS2800B12C4—Fluid Property Sensor Module," Dec. 2009. [www.meas-spec.com].

(Continued)

*Primary Examiner* — Arleen M Vazquez
*Assistant Examiner* — Alesa Allgood
(74) *Attorney, Agent, or Firm* — Cantor Colburn LLP

(57) ABSTRACT

Disclosed is an apparatus for estimating a property of a fluid. The apparatus includes: a piezoelectric resonator configured to be disposed in the fluid; an electrode embedded in the piezoelectric resonator and included in a resonator circuit configured to output an electrical signal related to the property; a discontinuity defined by a surface of the piezoelectric resonator, the discontinuity altering an impedance of the resonator circuit if a high-dielectric fluid or a conductive fluid is disposed in the discontinuity; and an insulating material disposed in the discontinuity.

21 Claims, 4 Drawing Sheets

(56) References Cited

U.S. PATENT DOCUMENTS

| | | |
|---|---|---|
| 6,494,079 B1 | 12/2002 | Matsiev et al. |
| 6,528,026 B2 | 3/2003 | Hajduk et al. |
| 6,818,183 B2 | 11/2004 | Hajduk et al. |
| 6,864,092 B1 | 3/2005 | Turner et al. |
| 6,873,916 B2 | 3/2005 | Kolosov et al. |
| 6,890,492 B1 | 5/2005 | Turner et al. |
| 6,904,786 B2 | 6/2005 | Matsiev et al. |
| 6,928,877 B2 | 8/2005 | Carlson et al. |
| 6,938,470 B2 | 9/2005 | DiFoggio et al. |
| 6,957,565 B2 | 10/2005 | Matsiev et al. |
| 7,043,969 B2 | 5/2006 | Matsiev et al. |
| 7,073,370 B2 | 7/2006 | Matsiev et al. |
| 7,158,897 B2 | 1/2007 | Kolosov et al. |
| 7,162,918 B2 | 1/2007 | DiFoggio et al. |
| 7,207,211 B2 | 4/2007 | Carlson et al. |
| 7,210,332 B2 | 5/2007 | Kolosov et al. |
| 7,225,081 B2 | 5/2007 | Kolosov et al. |
| 7,254,990 B2 | 8/2007 | Matsiev et al. |
| 7,272,525 B2 | 9/2007 | Bennett et al. |
| 7,302,830 B2 | 12/2007 | Kolosov et al. |
| 7,317,989 B2 | 1/2008 | DiFoggio et al. |
| 7,334,452 B2 | 2/2008 | Matsiev et al. |
| 7,350,367 B2 | 4/2008 | Matsiev et al. |
| 7,421,892 B2 | 9/2008 | DiFoggio et al. |
| 7,479,847 B2 | 1/2009 | Yamakawa et al. |
| 7,520,158 B2 | 4/2009 | DiFoggio |
| 7,562,557 B2 | 7/2009 | Bennett et al. |
| 7,603,889 B2 | 10/2009 | Cypes et al. |
| 7,634,937 B2 | 12/2009 | Burdett et al. |
| 7,647,965 B2 * | 1/2010 | Powell et al. ............ 166/250.01 |
| 7,677,183 B2 | 3/2010 | Borggaard |
| 7,694,734 B2 | 4/2010 | DiFoggio et al. |
| 7,721,590 B2 | 5/2010 | Kolosov et al. |
| 2002/0063497 A1 * | 5/2002 | Panasik ........................ 310/364 |
| 2002/0178787 A1 | 12/2002 | Matsiev et al. |
| 2003/0041653 A1 | 3/2003 | Matsiev et al. |
| 2004/0074302 A1 | 4/2004 | Matsiev et al. |
| 2004/0074303 A1 | 4/2004 | Matsiev et al. |
| 2004/0236512 A1 | 11/2004 | DiFoggio et al. |
| 2004/0244487 A1 | 12/2004 | Kolosov et al. |
| 2004/0250622 A1 | 12/2004 | Kolosov et al. |
| 2005/0149276 A1 | 7/2005 | Kolosov et al. |
| 2005/0180680 A1 * | 8/2005 | Kong .............................. 385/14 |
| 2005/0209796 A1 | 9/2005 | Kolosov et al. |
| 2005/0247119 A1 | 11/2005 | DiFoggio et al. |
| 2005/0262944 A1 * | 12/2005 | Bennett et al. .................. 73/592 |
| 2006/0082261 A1 | 4/2006 | Tanaya |
| 2007/0095535 A1 | 5/2007 | DiFoggio et al. |
| 2007/0113639 A1 | 5/2007 | DiFoggio et al. |
| 2007/0175632 A1 | 8/2007 | Powell et al. |
| 2007/0251296 A1 | 11/2007 | DiFoggio |
| 2008/0215245 A1 | 9/2008 | Reittinger |
| 2009/0100925 A1 | 4/2009 | DiFoggio et al. |
| 2009/0120169 A1 | 5/2009 | Chandler, Jr. et al. |
| 2009/0133470 A1 | 5/2009 | Whalen |

OTHER PUBLICATIONS

Matsiev, L.F., J.W. Bennet and E.W. McFarland. "Application of Low Frequency Mechanical Resonators to Liquid Property Measurements," IEEE Ultrasonics Symposium, 1998.

Matsiev, L. F. "Application of Flexural Mechanical Resonators to Simultaneous Measurements of Liquid Density and Viscosity," Ultrasonics Symposium 1999, pp. 457-460.

Matsiev, L.F. "Application of Flexural Mechanical Resonators to High Throughput Liquid Characterization," Ultrasonics Symposium, Oct. 22-25, 2000.

Notification of Transmittal of the International Search Report and the Written Opinion of the International Searching Authority, or the Declaration; PCT/US2011/039597; Feb. 9, 2012.

Atul Saluja, and Devendra S. Kalonia. "Measurement of Fluid Viscosity at Microliter Volumes Using Quartz Impedance Analysis" AAPS PharmSciTech 2004; 5 (3) Article 47. Submitted: Apr. 21, 2004; Accepted: Aug. 5, 2004.

Notification of Transmittal of the International Search Report and the Written Opinion of the International Searching Authority, or the Declaration; PCT/US2012/046355; Jan. 29, 2013.

* cited by examiner

METHOD FOR TREATING AND SEALING PIEZOELECTRIC TUNING FORKS

CROSS REFERENCE TO RELATED APPLICATIONS

This application claims the benefit of an earlier filing date from U.S. Provisional Application Ser. No. 61/353,816 filed Jun. 11, 2010, the entire disclosure of which is incorporated herein by reference.

BACKGROUND

1. Field of the Invention

The present invention relates to the field of downhole fluid analysis. More particularly, the present invention relates to a method of sealing piezoelectric resonators.

2. Description of the Related Art

There is considerable interest in obtaining density and viscosity for fluids downhole at conditions of high temperature and pressure. One technique to obtain density and viscosity measurements of fluids downhole is to dispose a piezoelectric resonator such as a tuning fork in a borehole where the fluids are sampled. The tuning fork is immersed in a downhole fluid having properties that affect the resonance of the tuning fork.

One type of tuning fork is made from a piezoelectric crystal in contact with two electrodes. By sweeping the frequency of an electric signal applied to the electrodes, a real impedance peak and an imaginary impedance peak of the immersed tuning fork can be measured. The peaks can then be correlated to characteristics of the fluid such as density and viscosity.

Unfortunately, manufacturing defects can alter the response characteristics of piezoelectric resonators making them unusable or decreasing their accuracy.

BRIEF SUMMARY

Disclosed is an apparatus for estimating a property of a fluid. The apparatus includes: a piezoelectric resonator configured to be disposed in the fluid; an electrode embedded in the piezoelectric resonator and included in a resonator circuit configured to output an electrical signal related to the property; a discontinuity defined by a surface of the piezoelectric resonator, the discontinuity altering an impedance of the resonator circuit if a high-dielectric fluid or a conductive fluid is disposed in the discontinuity; and an insulating material disposed in the discontinuity.

Also disclosed is a method for estimating a property of a fluid, the method includes: disposing a piezoelectric resonator in a fluid wherein an electrode included in a resonator circuit is embedded in the piezoelectric resonator, the piezoelectric resonator having a discontinuity configured to alter an impedance of the resonator circuit if a high-dielectric fluid or a conductive fluid is disposed in the discontinuity; using the resonator circuit to resonate the piezoelectric resonator; and obtaining a signal related to the property from the resonator circuit; wherein an insulating material is disposed in the discontinuity.

Further disclosed is a method for producing a piezoelectric resonator, the method comprising: disposing an insulating material in a discontinuity defined by a surface of the piezoelectric resonator; and removing the insulating material from a surface of the piezoelectric resonator not intended to be sealed with the insulating material.

Further disclosed is a piezoelectric resonator for estimating a property of a fluid, the resonator includes an electrode embedded in piezoelectric material and configured to output a signal responsive to the property; and an insulating material disposed in a discontinuity defined by a surface of the piezoelectric material, the discontinuity altering the signal if a high-dielectric fluid or a conductive fluid is disposed in the discontinuity without the insulating material in the discontinuity.

BRIEF DESCRIPTION OF THE DRAWINGS

The subject matter, which is regarded as the invention, is particularly pointed out and distinctly claimed in the claims at the conclusion of the specification. The foregoing and other features and advantages of the invention are apparent from the following detailed description taken in conjunction with the accompanying drawings, wherein like elements are numbered alike, in which:

DETAILED DESCRIPTION

Figure 1:
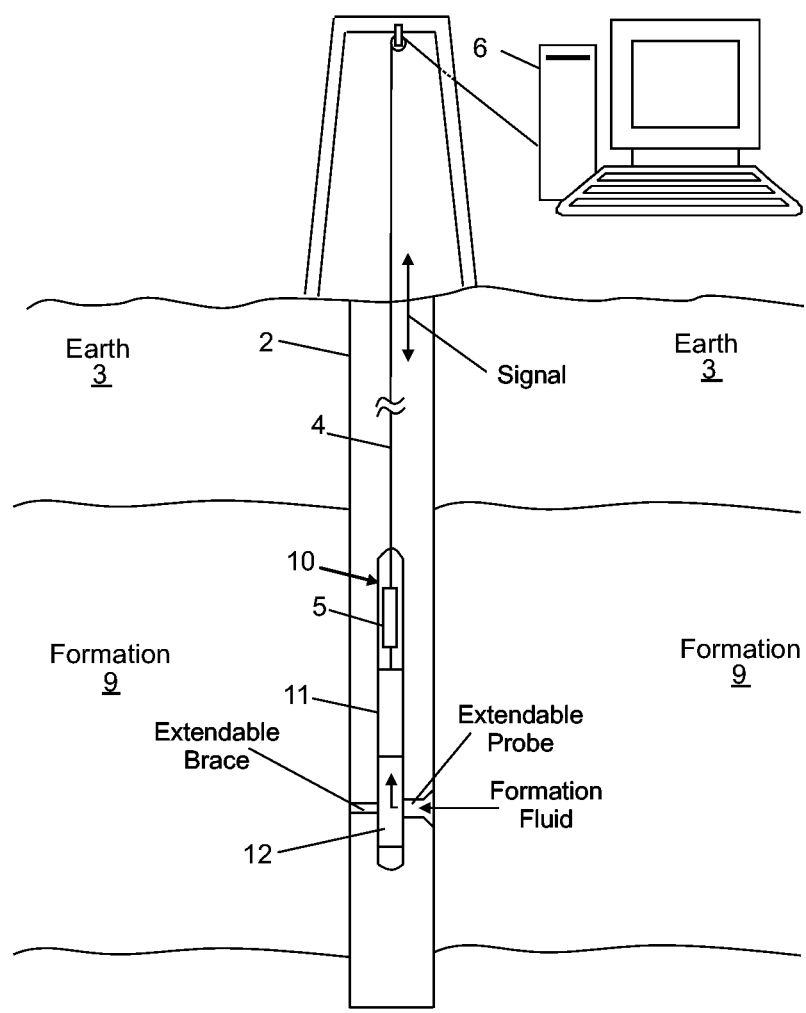
FIG. 1 illustrates an exemplary embodiment of a downhole tool disposed in a borehole penetrating the earth.

Piezoelectric resonators are used to estimate properties of fluids downhole. The resonators are used to provide a signal that is correlated to a property of the fluid being estimated. During fabrication of the piezoelectric resonators, one or more discontinuities, such as cracks or flaws in the seams of bonds between parts of the resonator, may occur and reach the surface of the piezoelectric resonator. If a conductive fluid or a fluid with a high dielectric constant (e.g., water or water-containing oil) enters the discontinuity, the signal can be diminished so that the corresponding estimates of fluid properties are less accurate or less precise.

Disclosed are exemplary embodiments of techniques for treating piezoelectric resonators that have one or more discontinuities reaching a surface exposed to fluids downhole. The techniques call for disposing an insulating material such as an insulating liquid in the discontinuities wherein the insulating material is suitable for high temperature use and is immiscible in either oil or water. The insulating liquid is further selected to have an affinity to wet the piezoelectric resonator better than water or oil, which may be encountered in a downhole environment. Hence, with the insulating liquid disposed in the discontinuities, water or oil will tend not to displace the insulating liquid.

Before the techniques are discussed in detail, certain definitions are provided. The term "piezoelectric resonator" relates to any piezoelectric material that can be excited electrically at or around its resonant frequency. The resonator is coupled to one or more electrodes, which are used to form an electrical circuit with the resonator. With the resonator immersed in a fluid of interest, a resonator circuit sweeps a frequency of a voltage applied to the resonator and a signal is obtained that is correlated to a property of the fluid of interest. In general, the piezoelectric resonator is fabricated from a piezoelectric material.

The term "discontinuity" relates to any crack, fissure, or depression in a surface of the piezoelectric resonator that is exposed to a fluid downhole. The discontinuity is of a dimension that can allow a liquid to enter. The discontinuity can partially penetrate the surface or completely penetrate the surface to an embedded or coupled electrode. When the discontinuity partially penetrates the surface, a conductive fluid or a fluid with a high dielectric constant disposed in the discontinuity can alter the alternating current (AC) impedance of the electrical circuit formed by the resonator. When the discontinuity completely penetrates the surface and electrically connects the two internal electrodes embedded in the piezoelectric resonator, a conductive fluid disposed in the discontinuity can alter the direct current (DC) impedance of the electrical circuit formed by the resonator.

The term "insulating material" relates to a material that is configured to insulate against the conduction of electricity. The insulating material is generally a liquid that is configured to fill and seal a discontinuity. The liquid may remain in a liquid state and be referred to as an "insulating liquid" or the liquid may be solidified after filling the discontinuity. The insulating material has a dielectric constant low enough to so that when the insulating material fills a discontinuity, the discontinuity will not significantly affect the electrical impedance formed by the piezoelectric resonator resonating in a fluid of interest.

In general, the insulating material has a dielectric constant that is much less than the dielectric constant of water. It is understood that the dielectric constant of a material varies with temperature and frequency at which the dielectric constant is measured. Typical values of the dielectric constant for some liquids are 80 for water and 1.8-2.6 for pure crude oil. Crude oil that is encountered downhole often has 1-2% water by volume contained in it, which raises its effective dielectric constant. A dielectric constant less than or equal to 10 is considered to be "much less" than the dielectric constant of water. Hence, a "low dielectric material" refers to a material having a dielectric constant that is much less than the dielectric constant of water. A "high dielectric material" is defined as a material having a dielectric constant that is comparable to or greater than the dielectric constant of water.

Reference may now be had to FIG. 1, which illustrates an embodiment of a downhole tool 10 disposed in a borehole 2 penetrating the earth 3. The earth 3 includes a formation 9, which contains a formation fluid of interest. The downhole tool 10 is configured to perform a measurement of a property of a fluid downhole using a piezoelectric resonator 11. The downhole tool 10 is supported and conveyed through the borehole 2 by a carrier 4. In the embodiment of FIG. 1, the carrier 4 is an armored wire line. In logging-while-drilling (LWD or measurement-while-drilling (MWD) applications, the carrier 4 can be a drill string. The wireline 4 can also provide communications capability between downhole electronics 5 and a surface computer processing system 6.

Still referring to FIG. 1, the downhole tool 10 includes a formation fluid tester 12. The formation fluid tester 12 is configured to extract the formation fluid from the earth formation 9. Once the formation fluid is extracted, the piezoelectric resonator 11 is immersed in the extracted fluid to perform a measurement of a property of the fluid. In another embodiment, the piezoelectric resonator 11 is immersed in a borehole fluid to measure a property of the borehole fluid.

Figure 2:
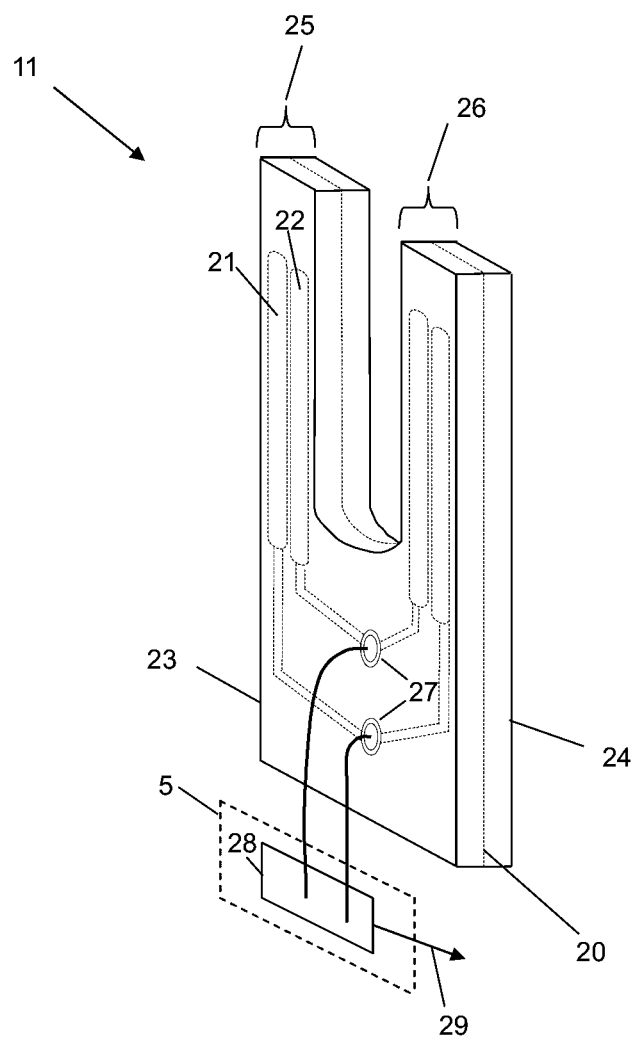
FIG. 2 depicts aspects of a piezoelectric resonator configured as a tuning fork disposed at the downhole tool.

Reference may now be had to FIG. 2, which depicts aspects of the piezoelectric resonator 11. FIG. 2 illustrates a top cross-sectional view of one embodiment of the piezoelectric resonator 11. In the embodiment of FIG. 2, the resonator 11 is a tuning fork and may be referred to as the tuning fork 11. The tuning fork 11 is embedded with a first electrode 21 and a second electrode 22. In one embodiment, a section of each of the electrodes 21 and 22 may be embedded in a first tine 25 and a second tine 26. In one embodiment, the electrodes 21 and 22 are made of a gold foil. The embedded electrode design prevents the electrodes from being worn off by passing sand or corroded off by acids or other chemicals in the downhole fluids. The tuning fork 11 is made from a piezoelectric material such as lithium niobate. In one or more embodiments, when a voltage with a sweeping frequency is applied to the electrodes 21 and 22, the tuning fork 11 resonates at a frequency related to a property of the fluid in which the tuning fork 11 is immersed. In one or more embodiments, the electrical impedance of the tuning fork 11 resonating in the fluid of interest is related to a property of that fluid. Downhole electronics 5 include a resonator circuit 28 configured to electrically excite the tuning fork 11 by applying a voltage with a sweeping frequency and to provide an electrical signal 29 comprising a value of the property such as density and/or viscosity.

Still referring to FIG. 2, the tuning fork 11 includes a first tuning fork section 23 and a second tuning fork section 24. The electrodes 21 and 22 are embedded between the tuning fork sections 23 and 24. The tuning fork sections 23 and 24 are bonded together with a bond 20 to form the tuning fork 11 and embed the electrodes 21 and 22.

Still referring to FIG. 2, the tuning fork 11 includes elastomeric seals 27 configured to seal the electrodes 21 and 22.

Figure 3:
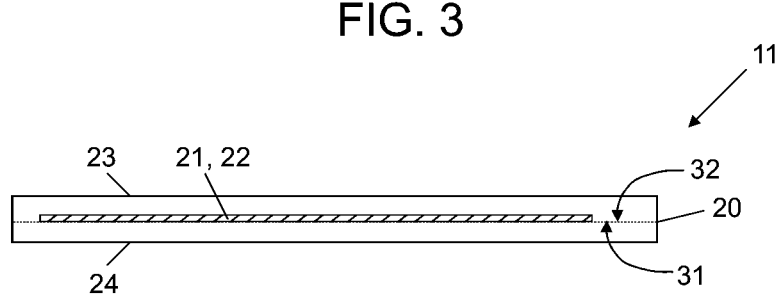
FIG. 3 depicts aspects of the tuning fork.

Reference may now be had to FIG. 3, which illustrates a side cross-sectional side view of the tuning fork 11. As shown in FIG. 3, the tuning fork 11 includes the bond 20 that bonds a first surface 31 of the first tuning fork section 23 to a second surface 32 of the second tuning fork section 24 such that the surfaces 31 and 32 touch. In one embodiment, the bond 20 can include a bond discontinuity. The bond discontinuity can be partially invasive or it can invade completely to the electrode 21 and/or the electrode 22.

Figure 4:
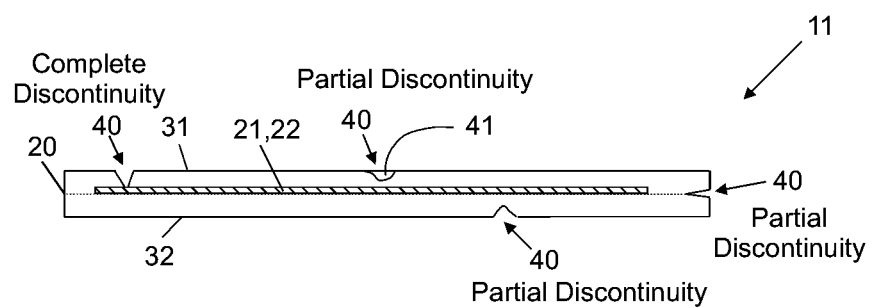
FIG. 4 depicts aspects of discontinuities defined by a surface in the piezoelectric resonator.

Reference may now be had to FIG. 4, which depicts aspects of discontinuities 40. FIG. 4 illustrates magnified examples of partial discontinuities 40 which do not reach the electrode 21 or 22 and a complete discontinuity 40 which reaches the electrode 21 or 22. Also shown is an insulating material 41 disposed in one of the discontinuities 40.

In one embodiment, the insulating material 41 is a perfluorinated polyether such as FOMBLIN®. FOMBLIN® is available from Solvay Plastics of Brussels, Belgium. Experiments have shown that FOMBLIN®, a liquid, wets lithium niobate better than does water or oil. Hence, FOMBLIN® will stay in the discontinuities 40 and not be displaced by water or oil. FOMBLIN® is also a high temperature fluid that is often used as a vacuum pump oil because FOMBLIN® has a very low vapor pressure, which is generally below a few millionths of atmospheric pressure at 100 degrees C. Therefore, FOMBLIN® will not be evaporated away by heat. FOMBLIN® is also immiscible in either oil or water.

FOMBLIN® may also be used to seal a surface of the elastomeric seals 27 to prevent diffusion of sodium ions from brine into the elastomer. Such diffusion can lead to an increase in the capacitance of the tuning fork 11 and a corresponding loss of signal.

In one embodiment, the insulating material 41 is a ceramic grout or sodium silicate in water, which is known as "water glass". The ceramic grout or water glass has liquid or paste-like properties when disposed in a discontinuity 40 under pressure. After treatment, the surfaces of the tuning fork 11 are wiped clean and then heated in an oven to convert the water glass or ceramic grout to an insoluble glass or ceramic.

Figure 5:
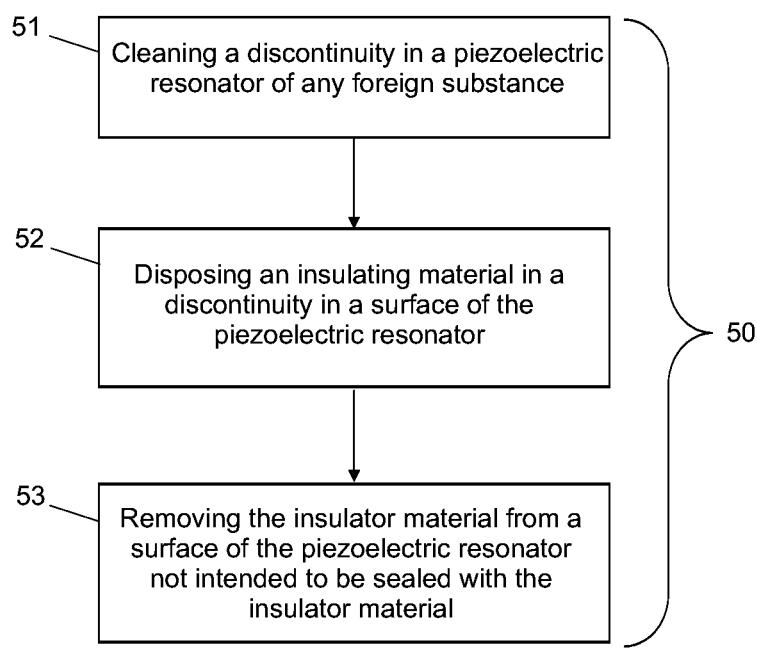
FIG. 5 presents one example of a method for producing the piezoelectric resonator.

FIG. 5 presents one example of a method 50 for sealing a discontinuity in a surface of the piezoelectric resonator 11. The method 50 calls for (step 51) cleaning the discontinuity of any foreign substance that may be disposed in the discontinuity. Step 51 can include cleaning with one or more cleaning agents and flushing with one or more flushing agents such as water. Step 51 can also include drying the discontinuity. In one embodiment, heat is used to dry the discontinuity. Further, the method 50 calls for (step 52) disposing the insulating material into a discontinuity in the piezoelectric resonator. Step 52 can include any or all of the following sub-steps: (a) disposing the piezoelectric resonator in a pressure chamber; (b) pulling a vacuum on the pressure chamber to remove substantially all the air; (c) back-filling the pressure chamber with the insulating material; (d) applying pressure to the insulating material with the pressure chamber; and (e) removing the piezoelectric resonator from the pressure chamber in order to remove excess insulating liquid from a surface of the piezoelectric resonator. Further, the method 50 calls for (step 53) removing the insulating material from a surface of the piezoelectric resonator not intended to be sealed with the insulating material. When the insulating material is water glass or ceramic grout, the method 50 can also include the further step of heating the piezoelectric resonator to convert the water glass or ceramic grout to an insoluble glass or ceramic.

Various other components may be included and called upon for providing for aspects of the teachings herein. For example, cleaning agents, flushing agents, drying apparatus, heating apparatus, inspection apparatus and testing apparatus may be included in support of the various aspects discussed herein or in support of other functions beyond this disclosure.

The term "carrier" as used herein means any device, device component, combination of devices, media and/or member that may be used to convey, house, support or otherwise facilitate the use of another device, device component, combination of devices, media and/or member. Other exemplary non-limiting carriers include drill strings of the coiled tube type, of the jointed pipe type and any combination or portion thereof. Other carrier examples include casing pipes, wirelines, wireline sondes, slickline sondes, drop shots, bottom-hole-assemblies, drill string inserts, modules, internal housings and substrate portions thereof.

Elements of the embodiments have been introduced with either the articles "a" or "an." The articles are intended to mean that there are one or more of the elements. The terms "including" and "having" are intended to be inclusive such that there may be additional elements other than the elements listed. The conjunction "or" when used with a list of at least two terms is intended to mean any term or combination of terms. The terms "first" and "second" are used to distinguish elements and are not used to denote a particular order. The term "couple" relates to coupling a first component to a second component either directly or indirectly through an intermediate component.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An apparatus for estimating a property of a fluid, the apparatus comprising:
   a piezoelectric resonator configured to be disposed in the fluid;
   an electrode embedded in the piezoelectric resonator and included in a resonator circuit configured to output an electrical signal related to the property;
   a discontinuity defined by a surface of the piezoelectric resonator, the discontinuity altering an impedance of the resonator circuit if a high-dielectric fluid or a conductive fluid is disposed in the discontinuity; and
   an insulating material disposed in the discontinuity;
   wherein the insulating material is a liquid configured to wet to the piezoelectric resonator better than water or oil.

2. The apparatus of claim 1, wherein the insulating material comprises a low dielectric constant.

3. The apparatus of claim 1, wherein the piezoelectric resonator is made of lithium niobate.

4. The apparatus of claim 1, wherein the insulating material comprises a perfluorinated polyether.

5. The apparatus of claim 1, wherein the property comprises at least one of density and viscosity.

6. The apparatus of claim 1, wherein the discontinuity comprises at least one of a crack, a fissure, and a depression.

7. The apparatus of claim 6, wherein the discontinuity penetrates to the electrode.

8. The apparatus of claim 1, wherein the piezoelectric resonator comprises a tuning fork, wherein the tuning fork comprises a first tuning fork section having a first surface and a second tuning fork section having a second surface, wherein the electrode is embedded between the first section and the second section, and wherein the tuning fork further comprises a bond between the first surface and the second surface.

9. The apparatus of claim 8, wherein the bond comprises the discontinuity.

10. The apparatus of claim 1, further comprising:
    a carrier configured to be conveyed through a borehole penetrating the earth;
    wherein the piezoelectric resonator is disposed at the carrier.

11. The apparatus of claim 10, wherein the fluid is a downhole fluid.

12. The apparatus of claim 10, wherein the carrier comprises at least one of a wireline, a slickline, a drill string, and coiled tubing.

13. A method for estimating a property of a fluid, the method comprising:
    disposing a piezoelectric resonator in a fluid wherein an electrode included in a resonator circuit is embedded in the piezoelectric resonator, the piezoelectric resonator comprising a discontinuity configured to alter an impedance of the resonator circuit if a high-dielectric fluid or a conductive fluid is disposed in the discontinuity;
    using the resonator circuit to resonate the piezoelectric resonator; and
    obtaining a signal related to the property from the resonator circuit;
    wherein an insulating material is disposed in the discontinuity, the insulating material being a liquid configured to wet to the piezoelectric resonator better than water or oil.

14. The method of claim 13, wherein the piezoelectric resonator is made of lithium niobate.

15. The method of claim 13, wherein the insulating material comprises a low dielectric constant.

16. The method of claim 13, wherein the piezoelectric resonator comprises a tuning fork, wherein the tuning fork comprises a first tuning fork section having a first surface and a second tuning fork section having a second surface, wherein the electrode is embedded between the first section and the second section, and wherein the tuning fork further comprises a bond between the first surface and the second surface.

17. The method of claim 16, wherein the bond comprises the discontinuity.

18. A method for producing a piezoelectric resonator, the method comprising: disposing an insulating material in a discontinuity in a surface of the piezoelectric resonator, wherein the discontinuity is defined by a surface of the piezoelectric resonator, the discontinuity altering an impedance of the resonator circuit if a high-dielectric fluid or a conductive fluid is disposed in the discontinuity; and removing the insulating material from a surface of the piezoelectric resonator not intended to be sealed with the insulating material; wherein the insulating material is a liquid configured to wet to the piezoelectric resonator better than water or oil.

19. The method of claim 18, further comprising cleaning the discontinuity prior to the disposing.

20. The method of claim 18, wherein the insulating material comprises a perfluorinated polyether.

21. A piezoelectric resonator for estimating a property of a fluid, the resonator comprising:
an electrode embedded in piezoelectric material and configured to output a signal responsive to the property; and
an insulating material disposed in a discontinuity defined by a surface of the piezoelectric material, the discontinuity altering the signal if a high-dielectric fluid or a conductive fluid is disposed in the discontinuity without the insulating material in the discontinuity;
wherein the insulating material is a liquid configured to wet to the piezoelectric resonator better than water or oil.

* * * * *